(12) United States Patent
Sors et al.

(10) Patent No.: US 8,921,409 B2
(45) Date of Patent: Dec. 30, 2014

(54) COMBINATION OF 4-{3-[CIS-HEXAHYDROCYCLOPENTA[C]PYRROL-2(1H)-YL]PROPOXY}BENZAMIDE AND A NMDA RECEPTOR ANTAGONIST AND PHARMACEUTICAL COMPOSITIONS CONTAINING THE SAME

(71) Applicant: Les Laboratoires Servier, Suresnes Cedex (FR)

(72) Inventors: Aurore Sors, Paris (FR); Caryn Trocme-Thibierge, Bois Colombes (FR); Annette Merdes, Munich (DE)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/706,828

(22) Filed: Dec. 6, 2012

(65) Prior Publication Data

US 2013/0150421 A1 Jun. 13, 2013

(30) Foreign Application Priority Data

Dec. 9, 2011 (FR) ...................................... 11 03777

(51) Int. Cl.
*A01N 43/38* (2006.01)
*A61K 31/40* (2006.01)
*A01N 43/00* (2006.01)
*A01N 43/46* (2006.01)
*A61K 31/55* (2006.01)

(52) U.S. Cl.
USPC .......................................... 514/412; 514/215

(58) Field of Classification Search
USPC ........................................................ 514/412
See application file for complete search history.

(56) References Cited

U.S. PATENT DOCUMENTS

| | | | |
|---|---|---|---|
| 7,432,280 B2 * | 10/2008 | Beadle et al. | 514/305 |
| 7,576,120 B2 * | 8/2009 | Casara et al. | 514/412 |
| 2007/0197625 A1 | 8/2007 | Casara et al. | |

FOREIGN PATENT DOCUMENTS

| | | |
|---|---|---|
| FR | 2866647 | 8/2005 |
| FR | 2953515 | 6/2011 |
| WO | 2005/092009 | 10/2005 |
| WO | 2010043787 | 4/2010 |

OTHER PUBLICATIONS

Sonkusare et al. (Dementia of Alzheimer's disease and other neurodegenerative disorders—memantine, a new hope Pharmacological Research. vol. 51, Issue 1, Jan. 2005, pp. 1-17).*
French Preliminary Search Report for FR1103777 of Jul. 17, 2012.
J.M. Witkin, et al., Pharmacology and Therapeutics, vol. 103, p. 1-20, Jan. 1, 2004.
P. Schmitt H., Psychopharmacology, vol. 179, No. 1, p. 151-153, Apr. 1, 2005.

* cited by examiner

*Primary Examiner* — Layla Soroush
(74) *Attorney, Agent, or Firm* — Hueschen and Sage

(57) ABSTRACT

Combination between 4-{3-[cis-hexahydrocyclopenta[c]pyrrol-2(1H)-yl]propoxy}-benzamide of formula (I):

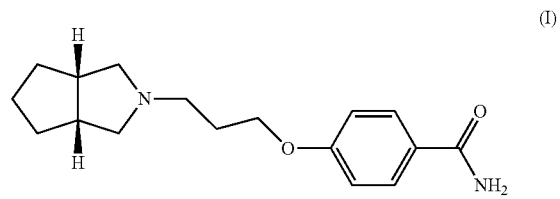

or an addition salt thereof with a pharmaceutically acceptable acid or base, and an NMDA glutamatergic receptor antagonist.

Medicinal products containing the same which are useful in the treatment of cognitive disturbances associated with cerebral ageing and neurodegenerative diseases.

6 Claims, 2 Drawing Sheets

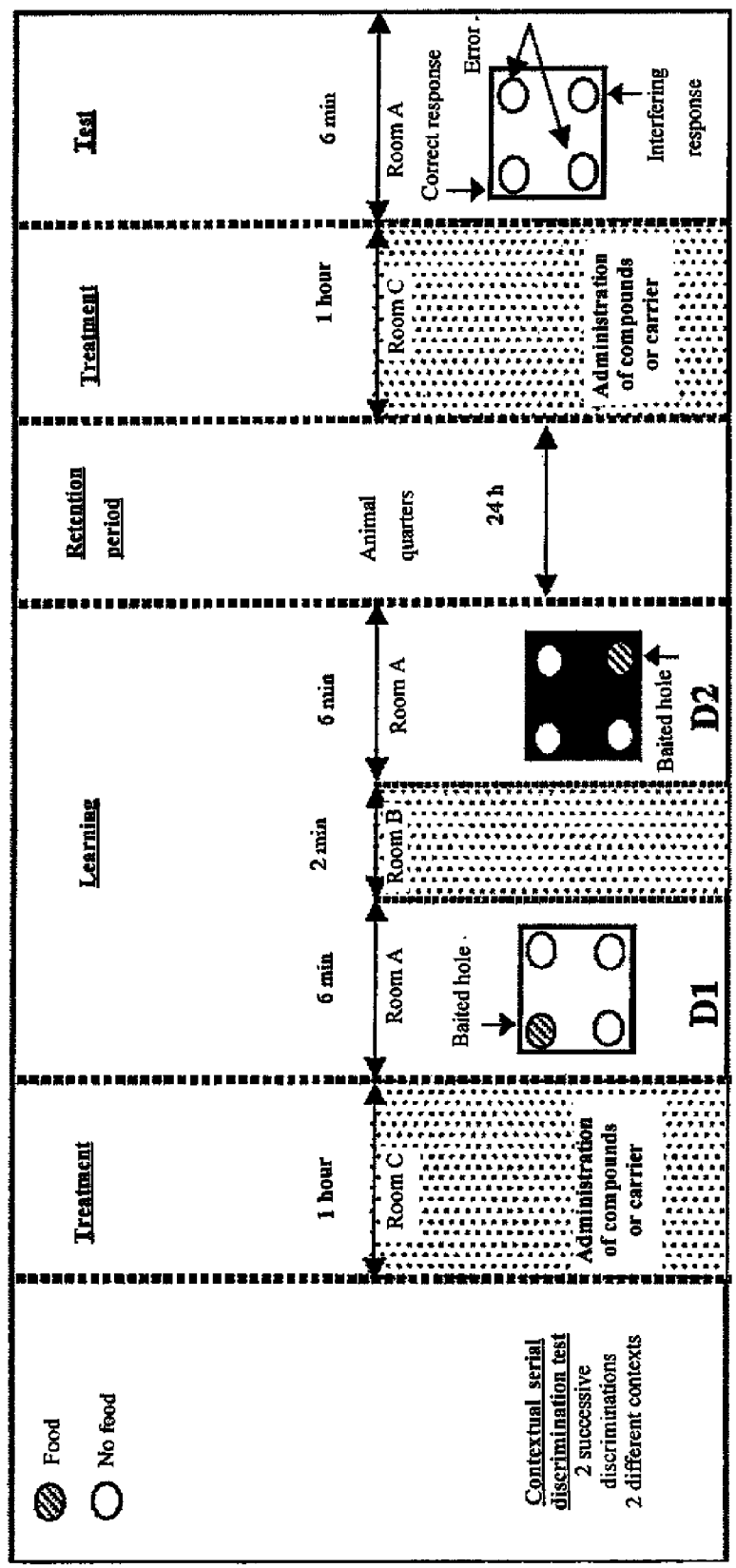
Figure 1. Procedure.
(modified, after Tronche et al., 2010)

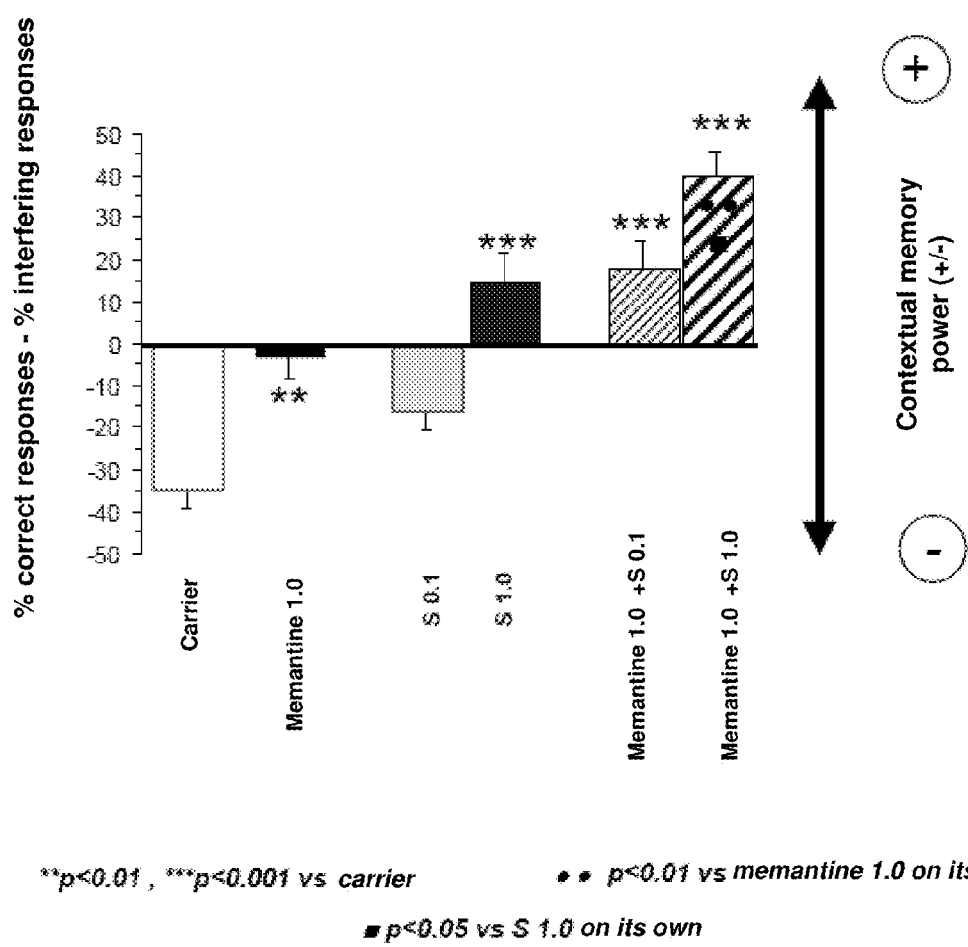
Figure 2. Power of contextual memory.

COMBINATION OF 4-{3-[CIS-HEXAHYDROCYCLOPENTA[C] PYRROL-2(1H)-YL]PROPOXY}BENZAMIDE AND A NMDA RECEPTOR ANTAGONIST AND PHARMACEUTICAL COMPOSITIONS CONTAINING THE SAME

The present invention relates to a new combination between 4-{3-[cis-hexahydrocyclopenta[c]pyrrol-2(1H)-yl]propoxy}benzamide of formula (I):

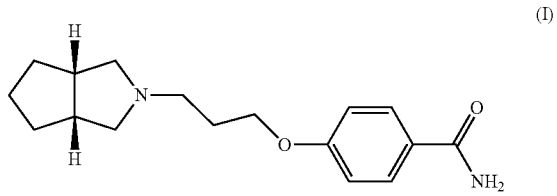 [SMILES: NC(=O)c1ccc(OCCCN2C[C@H]3CCC[C@H]3C2)cc1]

or an addition salt thereof with a pharmaceutically acceptable acid or base, and an NMDA (N-methyl-D-aspartate) glutamatergic receptor antagonist, for obtaining pharmaceutical compositions for use in the treatment of cognitive disturbances associated with cerebral ageing and with neurodegenerative diseases.

4-{3-[cis-Hexahydrocyclopenta[c]pyrrol-2(1H)-yl]propoxy}benzamide has the characteristic of interacting with central histaminergic systems in vivo. These properties provide it with activity in the central nervous system and, more especially, in the treatment of cognitive deficiencies associated with cerebral ageing and with neurodegenerative diseases.

4-{3-[cis-Hexahydrocyclopenta[c]pyrrol-2(1H)-yl]propoxy}benzamide, its preparation and its therapeutic use have been described in Patent Application WO2005/089747.

The Applicant has now found that 4-{3-[cis-hexahydrocyclopenta[c]pyrrol-2(1H)-yl]propoxy}benzamide of formula (I), or an addition salt thereof with a pharmaceutically acceptable acid or base, used in combination with an NMDA glutamatergic receptor antagonist has valuable properties for the treatment of cognitive disturbances associated with cerebral ageing and with neurodegenerative diseases.

Neurodegenerative diseases related to cerebral ageing such as Alzheimer's disease are characterised by disturbances of memory and cognitive dysfunction. The cognitive disturbances are usually associated with a reduction in the ability of neurons to synthesise and release certain neurotransmitters. There is moreover observed a progressive loss of synaptic plasticity and of neuronal processes, this neuronal loss being accelerated in certain specific regions of the brain. Among the various neurotransmitters, central histamine and acetylcholine play a crucial part in the control of cognitive functions (Witkin and Nelson, *Pharmacol. & Therap.*, 2004, 103, 1-20) and their levels have been shown to greatly diminish in the brains of patients suffering from Alzheimer's disease compared to those observed in healthy elderly people (Panula et al., *Neuroscience*, 1998, 82(4), 993-997). Type $H_3$ histaminergic receptors, which are especially abundant in the central nervous system, are mainly presynaptic modulators of neural transmission and are present in a variety of neuronal circuits relevant to cognition (Blandina et al., *Learn Mem.*, 2004, 11(1): 1-8). They act by negatively regulating the release of neurotransmitters such as histamine, acetylcholine, serotonin, noradrenaline and dopamine. Given that histaminergic neurons seem to be largely spared in Alzheimer's disease, compounds that are antagonists or inverse agonists of $H_3$ receptors could open the way to new treatments for the cognitive disturbances related to cerebral ageing.

Conversely, progressive degeneration of cholinergic neurons and dysfunction of glutamatergic neurotransmission are observed in the course of Alzheimer's disease. Targeting the glutamatergic system, especially the NMDA receptors, offers an alternative treatment approach to those medicaments that target solely the cholinergic system (i.e. acetylcholinesterase inhibitors). Memantine is a non-competitive antagonist of the NMDA receptor, of nicotinic receptors and of the $5HT_3$ serotoninergic receptor and also has a dopaminergic component (Lipton, *Nat Rev Drug Discov.*, 2006, 5(2): 160-70; Aracava et al., *J Pharmacol Exp Ther.*, 2005, 312(3): 1195-205; Rammes et al., *Neurosci Lett.*, 2001, 306: 81-84). Memantine is currently used in the symptomatic treatment of moderate to severe forms of Alzheimer's disease. Indeed, it has been shown that memantine, like antagonists/inverse agonists of $H_3$ receptors, makes it possible to improve cognitive performances in various animal models of episodic memory and working memory (Yuede et al., *Behav. Pharmacol.*, 2007, 18(5-6): 347-363). Improving cognitive functions may therefore be based on several types of strategy targeting especially either histamine or the glutamatergic system.

The present invention has shown, surprisingly, that the effects of NMDA glutamatergic receptor antagonists are potentiated by those of 4-{3-[cis-hexahydrocyclopenta[c]pyrrol-2(1H)-yl]propoxy}benzamide or addition salts thereof with a pharmaceutically acceptable acid or base. Accordingly, co-administration of these compounds could make it possible to improve the cognitive performances of patients compared to the simple administration of an NMDA glutamatergic receptor antagonist without, however, increasing the adverse effects associated with treatment with NMDA glutamatergic receptor antagonists (especially drowsiness, headaches, sensations of dizziness, hypertension, dyspnoea or constipation). In other words, treatments associating 4-{3-[cis-hexahydrocyclopenta[c]pyrrol-2(1H)-yl]propoxy}benzamide with therapeutic doses of NMDA receptor antagonists that are lower than those customarily used in mono-therapy can therefore now be envisaged, with equivalent or even superior cognitive performances and fewer adverse effects.

This unforeseeable effect makes it possible to envisage using a combination between 4-{3-[cis-hexahydrocyclopenta[c]pyrrol-2(1H)-yl]propoxy}benzamide, or an addition salt thereof, and an NMDA receptor antagonist in the treatment of cognitive disturbances associated with cerebral ageing and with neurodegenerative diseases. The cognitive disturbances associated with Alzheimer's disease are being especially targeted.

4-{3-[cis-Hexahydrocyclopenta[c]pyrrol-2(1H)-yl]propoxy}benzamide is used preferably in the form of an oxalate or hydrochloride within the context of the invention.

Among the NMDA receptor antagonists according to the invention there may be mentioned memantine, L-4-chlorokynurenine, 1-(2,2-diphenyltetrahydrofuran-3-yl)-N,N-dimethylmethanamine (ANAVEX 2-73) and (5R,9R,11E)-5-amino-11-ethylidene-7-methyl-5,6,9,10-tetrahydro-5,9-methanocycloocta[b]pyridin-2(1H)-one (huperzine A). Memantine is especially preferred. Memantine is preferably used in the form of a hydrochloride.

The invention accordingly relates to use of the combination between 4-{3-[cis-hexahydrocyclopenta[c]pyrrol-2(1H)-yl]propoxy}benzamide, or addition salts thereof with a pharmaceutically acceptable acid or base, and an NMDA receptor antagonist in obtaining pharmaceutical compositions intended for the treatment of cognitive disturbances associated with cerebral ageing and with neurodegenerative diseases.

More especially, the combination of 4-{3-[cis-hexahydrocyclopenta[c]pyrrol-2(1H)-yl]propoxy}benzamide and memantine is used in the treatment of cognitive disturbances associated with Alzheimer's disease.

The invention relates also to pharmaceutical compositions comprising the combination between 4-{3-[cis-hexahydrocyclopenta[c]pyrrol-2(1H)-yl]propoxy}benzamide, or addition salts thereof with a pharmaceutically acceptable acid or base, and an NMDA receptor antagonist in combination with one or more pharmaceutically acceptable excipients.

In the pharmaceutical compositions according to the invention, the proportion of active ingredients by weight (weight of active ingredients over the total weight of the composition) is from 5 to 50%.

Among the pharmaceutical compositions according to the invention there will be more especially used those which are suitable for administration by the oral, parenteral and especially intravenous, per- or trans-cutaneous, nasal, rectal, perlingual, ocular or respiratory route, more specifically tablets, dragées, sublingual tablets, hard gelatin capsules, glossettes, capsules, lozenges, injectable preparations, aerosols, eye or nose drops, suppositories, creams, ointments, dermal gels etc.

Besides 4-{3-[cis-hexahydrocyclopenta[c]pyrrol-2(1H)-yl]propoxy}benzamide and the NMDA receptor antagonist compound, the pharmaceutical compositions according to the invention comprise one or more excipients or carriers selected from diluents, lubricants, binders, disintegration agents, stabilisers, preservatives, absorbents, colourants, sweeteners, flavourings etc.

By Way of Non-Limiting Example there May be Mentioned:
  as diluents: lactose, dextrose, sucrose, mannitol, sorbitol, cellulose, glycerol,
  as lubricants: silica, talc, stearic acid and its magnesium and calcium salts, polyethylene glycol,
  as binders: magnesium aluminium silicate, starch, gelatin, tragacanth, methylcellulose, sodium carboxymethylcellulose and polyvinylpyrrolidone,
  as disintegrants: agar, alginic acid and its sodium salt, effervescent mixtures.

The compounds of the combination may be administered simultaneously or sequentially. The administration route is preferably the oral route, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

Preference is given to the pharmaceutical compositions being tablets.

The useful dosage regimen varies according to the sex, age and weight of the patient, the administration route, the nature of the disorder and of any associated treatments and ranges from 0.5 mg to 100 mg of 4-{3-[cis-hexahydrocyclopenta[c]pyrrol-2(1H)-yl]propoxy}benzamide per 24 hours, more preferably 2 mg, 5 mg or 20 mg (expressed in terms of base equivalent) per day. The dose of the NMDA receptor antagonist will be the same as or less than that used when it is administered on its own. In the case of memantine, the dosage regimen is from 1 mg to 20 mg per day, preferred daily doses being 10 and 20 mg for memantine hydrochloride.

In preferred embodiments of the invention, the combination between 4-{3-[cis-hexahydrocyclopenta[c]pyrrol-2(1H)-yl]propoxy}benzamide (compound S) and memantine is administered at the following doses:

|  | Composition 1 | Composition 2 | Composition 3 |
|---|---|---|---|
| Hydrochloride of compound S | 2.25 mg (or 2 mg of base equivalent) | 5.63 mg (or 5 mg of base equivalent) | 22.52 mg (or 20 mg of base equivalent) |
| Memantine hydrochloride | 10 mg | 10 mg | 10 mg |

|  | Composition 4 | Composition 5 | Composition 6 |
|---|---|---|---|
| Hydrochloride of compound S | 2.25 mg (or 2 mg of base equivalent) | 5.63 mg (or 5 mg of base equivalent) | 22.52 mg (or 20 mg of base equivalent) |
| Memantine hydrochloride | 20 mg | 20 mg | 20 mg |

Pharmaceutical Composition:

Formula for the preparation of 1000 tablets each containing 5.63 mg of 4-{3-[cis-hexahydrocyclopenta[c]pyrrol-2(1H)-yl]propoxy}benzamide hydrochloride (corresponding to 5 mg of base equivalent) and 10 mg of memantine hydrochloride:

4-{3-[cis-hexahydrocyclopenta[c]pyrrol-2(1H)-yl]propoxy}benzamide hydrochloride ... 5.63 g
Memantine hydrochloride ... 10 g
Maize starch ... 20 g
Maltodextrin ... 7.5 g
Colloidal silica ... 0.2 g
Sodium starch glycolate ... 3 g
Magnesium stearate ... 1 g
Lactose ... 55 g

EXAMPLE A

Experiment in a Model of Episodic Memory, the Contextual Serial Discrimination Test The effects of 4-{3-[cis-hexahydrocyclopenta[c]pyrrol-2(1H)-yl]propoxy}benzamide and memantine (both in the form of a hydrochloride), administered on their own or in combination, were studied using a contextual discrimination test in the middle-aged (14-15 months old) C57B16 mouse (n=12 per group) (Célérier et al., *Learn Mem.*, 2004, 11(2), 196-204; Tronche et al., *Behav. Brain Res.*, 2010, 215(2): 255-60). In this model, the middle-aged mice have a specific dysfunction of contextual episodic memory compared to young mice, without a deficiency in spatial memory. This model is relevant for evaluating the effects of products in Alzheimer's disease because patients suffering from that form of dementia also have disturbances of contextual episodic memory, this being the case from a very early stage (Gold and Budson, *Expert Rev Neurother.*, 2008, 8(12): 1879-1891).

The mice, placed in a box with raised edges, learn two types of consecutive spatial discrimination (D1: white floor, then D2: black floor) on a floor with four holes, in which just one of the holes is baited, the arrangement being opposite in D1 and in D2. The colour of the floor (black or white) constitutes the internal context specific to each discrimination. 24 hours after the learning step, the mice are returned to the white contextual floor, and the following are measured:
  the percentage of correct responses (i.e. % of lowering the head into the hole that was baited during the learning exercise on the white floor), the percentage of interfering responses (i.e. % of lowering the head into the hole that was baited during the learning exercise on the black floor, the last context presented to the mice), and the percentage of errors (i.e. % of lowering the head into the two holes that were not baited during learning, whether on the white floor or on the black floor (see FIG. 1).

The power of contextual memory is defined as being the difference between the percentage of correct responses and the percentage of interfering responses.

In this model it has been shown that, compared to young mice, the middle-aged mice have a contextual memory deficit due to the fact that the last context in which they learnt the location of the baited hole (i.e. the black floor) substantially interferes with memory of the baited hole in the first context presented during learning (i.e. the white floor). Because of this fact, the elderly mice have negative values for the power of contextual memory because the percentage of interfering responses is higher than the percentage of correct responses. In contrast, the young mice have a positive power of contextual memory (Tronche et al., *Behav. Brain Res.*, 2010, 215(2): 255-60).

The results of this study confirm the contextual memory deficit in middle-aged mice, the mice treated with the carrier of this experiment showing a negative contextual memory power of −34%. Following chronic treatment for 9 days with 4-{3-[cis-hexahydrocyclopenta[c]pyrrol-2(1H)-yl]propoxy}benzamide hydrochloride (0.1 mg/kg of base per os, the compound referred to as compound S in FIG. 2), no significant increase in the power of contextual memory is observed compared to the carrier (−15% versus −34%), the % of interfering responses remaining greater than the % of correct responses. Furthermore, the power of contextual memory increases slightly, compared to the carrier, following chronic treatment for 9 days with memantine hydrochloride at a dose of 1 mg/kg of base per os (−2% versus −34%) but is still negative (% of interfering responses>% of correct responses) giving rise to the possibility that the 1 mg/kg dose of memantine hydrochloride is a sub-active dose. In contrast, administration of the combination of 4-{3-[cis-hexahydrocyclopenta[c]pyrrol-2(1H)-yl]propoxy}benzamide (0.1 mg/kg of base per os) with memantine (sub-active dose of 1 mg/kg of base per os) leads to a substantial and significant increase in the power of contextual memory compared to the value obtained with the carrier on its own, the power of contextual memory then being positive (% of correct responses>% of interfering responses). These results show clear potentiation of the effects of sub-active dose memantine in the presence of an inactive dose of 4-{3-[cis-hexahydrocyclopenta[c]pyrrol-2(1H)-yl]propoxy}benzamide.

This potentiation is also confirmed when memantine (1 mg/kg of base per os) is associated with an active dose of 4-{3-[cis-hexahydrocyclopenta[c]pyrrol-2(1H)-yl]propoxy}benzamide (1 mg/kg of base per os): there is then observed a substantial increase in the memory performance of the treated mice compared to memantine on its own, which is statistically significant (power of contextual memory of +40%: the combination provides a very positive response versus a negative response of −2% for memantine on its own). This increase in the memory performance of mice treated with the combination is also confirmed compared to 4-{3-[cis-hexahydrocyclopenta[c]pyrrol-2(1H)-yl]propoxy}benzamide on its own (1 mg/kg of base per os) (power of contextual memory of +40% for the combination versus +14% for 4-{3-[cis-hexahydrocyclopenta[c]pyrrol-2(1H)-yl]propoxy}benzamide), this also being statistically significant. The increase in the power of contextual memory observed for the two combinations cannot be explained by simple addition of the effects of the compounds administered on their own, and shows synergistic activity for the two compounds when they are co-administered.

The results clearly demonstrate that the administration of these two compounds in combination makes it possible to obtain a substantial synergistic effect which is entirely unexpected. Pharmacokinetic analyses have moreover shown that there was no pharmacokinetic-type interaction between the two treatments which might justify or interfere with the synergistic effect described above.

In conclusion, the results presented hereinabove demonstrate synergistic activity between 4-{3-[cis-hexahydrocyclopenta[c]pyrrol-2(1H)-yl]propoxy}benzamide and memantine in terms of cognitive performances, this being the case without pharmacokinetic interaction.

BRIEF DESCRIPTION OF THE DRAWINGS

FIG. 1 shows the procedure described in Example A.
FIG. 2 shows the results of the procedure described in Example A.

The invention claimed is:

1. A composition comprising a combination of 0.5-100 mg of 4-{3-[cis-hexahydrocyclopenta[c]pyrrol-2(1H)-yl]propoxy}benzamide of formula (I):

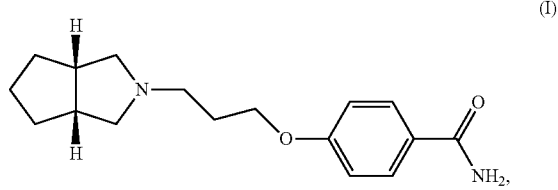 [SMILES: NC(=O)c1ccc(OCCCN2C[C@H]3CCC[C@H]3C2)cc1]

or an addition salt thereof with a pharmaceutically acceptable acid or base, and a sub-active dose of 1-20 mg of an NMDA glutamatergic receptor antagonist selected from memantine and pharmaceutically acceptable salts thereof.

2. The composition according to claim 1, wherein the 4-{3-[cis-hexahydrocyclopenta[c]pyrrol-2(1H)-yl]propoxy}benzamide is in the form of an oxalate or hydrochloride.

3. The composition according to claim 1, wherein the NMDA glutamatergic receptor antagonist is memantine hydrochloride.

4. The composition according to claim 1, wherein: (i) the 4-{3-[cis-hexahydrocyclopenta[c]pyrrol-2(1H)-yl]propoxy}benzamide is present at a dose of 2 mg, 5 mg or 20 mg (expressed in terms of base equivalent) in the form of a hydrochloride, and (ii) the NMDA glutamatergic receptor antagonist is memantine hydrochloride which is present at a dose of 10 mg or 20 mg.

5. A pharmaceutical composition comprising as active ingredient the composition according to claim 1, in combination with one or more pharmaceutically acceptable excipients.

6. The pharmaceutical composition according to claim 5, comprising 2 mg, 5 mg or 20 mg (expressed in terms of base equivalent) of 4-{3-[cis-hexahydrocyclopenta[c]pyrrol-2(1H)-yl]propoxy}benzamide in the form of a hydrochloride, and 10 mg or 20 mg of memantine hydrochloride as the NMDA glutamatergic receptor antagonist.

* * * * *